US005536262A

United States Patent [19]

Velasquez

[11] Patent Number: 5,536,262

[45] Date of Patent: Jul. 16, 1996

[54] MEDICAL COUPLING DEVICE

[75] Inventor: Gustavo G. Velasquez, Los Angeles, Calif.

[73] Assignee: Cedars-Sinai Medical Center, Los Angeles, Calif.

[21] Appl. No.: 301,611

[22] Filed: Sep. 7, 1994

[51] Int. Cl.[6] .................... A61M 37/00

[52] U.S. Cl. .................... 604/283; 604/86; 604/905

[58] Field of Search .................... 604/48, 52–57, 604/86, 93, 98, 192, 263, 283, 201, 905

[56] References Cited

U.S. PATENT DOCUMENTS

| | | |
|---|---|---|
| 2,661,740 | 12/1953 | Hickey . |
| 4,197,848 | 4/1980 | Garrett et al. . |
| 4,340,068 | 7/1982 | Kaufman . |
| 4,511,359 | 4/1985 | Vaillancourt . |
| 4,752,292 | 6/1988 | Lopez et al. . |
| 4,834,716 | 5/1989 | Ogle, II . |
| 4,883,483 | 11/1989 | Lindmayer . |
| 4,950,260 | 8/1990 | Bonaldo . |
| 4,981,469 | 1/1991 | Whitehouse et al. . |
| 5,033,476 | 7/1991 | Kasai . |
| 5,122,123 | 6/1992 | Vaillancourt . |
| 5,122,129 | 6/1992 | Olson et al. . |
| 5,135,489 | 8/1992 | Jepson et al. . |
| 5,139,483 | 8/1992 | Ryan . |
| 5,195,992 | 3/1993 | Dudar et al. . |
| 5,201,717 | 4/1993 | Wyatt et al. . |
| 5,360,423 | 11/1994 | McCormick . |

*Primary Examiner*—Randall L. Green
*Assistant Examiner*—Perry E. Van Over
*Attorney, Agent, or Firm*—Pretty, Schroeder, Brueggemann & Clark

[57] ABSTRACT

A medical coupling device is provided which is used for transferring fluid between a first reservoir and a second reservoir having a slit-less diaphragm. The device includes a connector having a port and a blunt cannula in fluid communication with the port. The cannula is adapted to puncture the diaphragm on the second reservoir and thereby facilitate the transfer of fluid between the first reservoir and the second reservoir. The cannula can be a hollow tube having an end which is substantially perpendicular to an axis extending longitudinally through the tube. The device may further include a shroud of a predetermined configuration associated with the connector. The shroud defines a recess for receiving the reservoir and inhibits inadvertent contact with the cannula which extends within the recess. The shroud defines a suction opening which tends to inhibit the formation of an undesirable suction upon removal of the reservoir. The shroud also defines a tapered sidewall which facilitates alignment of the reservoir with the cannula and guides the cannula into contact with the diaphragm.

22 Claims, 4 Drawing Sheets

10
12
18
21
24
29
33

MEDICAL COUPLING DEVICE

BACKGROUND OF THE INVENTION

This invention relates generally to devices for transferring fluid and, more particularly, to a medical coupling device which effectuates fluid transfer from one fluid reservoir to another in a manner that tends to avoid undesirable exposure to the fluid.

In the medical environment, it is often necessary or desirable to collect a sample of fluid, such as a liquid or gas, or to transfer a sample of such fluid from one reservoir to another while still preserving the integrity of the sample. For example, it is often desirable to collect a sample of blood from a patient and then transfer this sample to a reservoir, such as an evacuated tube or culture media container, for evaluation, testing or processing. A variety of devices have been developed that effectuate the collection and transfer of fluid between reservoirs. These include medical coupling devices and hypodermic needles.

Medical coupling devices employed for this purpose typically have a shroud or sheath which surrounds a pointed cannula or needle that in turn pierces an injection site on a rubber septum or diaphragm which is sealingly attached over an opening in the reservoir to which the fluid is to be transferred. The shroud also covers a sufficient portion of the reservoir such that the cannula or needle can properly pierce the injection site and transfer fluid to the reservoir from another reservoir to which the device is connected. While such devices effectuate fluid transfer between reservoirs, they do have disadvantages. Although the pointed cannula or needle is shielded by the shroud, the risk of accidental needlesticks still remains if, for example, a finger is inadvertently inserted into the open end of the shroud and contacts the pointed cannula or needle. Although the risk of accidental needlesticks has for many years been of concern to the medical community, it has been accentuated by the increasing prevalence of Acquired Immuno Deficiencies Syndrome (AIDS) among patients and the life threatening consequences associated with the unwanted transfer of the AIDS virus, hepatitis and other diseases.

The aforementioned disadvantage also tends to be exacerbated by the fact that medical coupling devices of this nature are used in combination of a variety of differently dimensioned and shaped reservoirs which the shroud needs to cover. It is also desirable that the shroud be large enough to permit the reservoir to come in contact with the needle so that the needle can pierce the injection site of the septum. There are, thus, constraints on the degree to which the shroud can be configured to reduce the risk of accidental needlesticks. Problems can also arise when the user attempts to disconnect and remove a reservoir which is large enough to engage the interior of the shroud, thereby creating a suction force which may need to be overcome during removal.

Other medical coupling devices also exist which utilize a cannula that is slidably received in a slit of an already pre-slit septum or diaphragm. These devices, however, are fundamentally incompatible with the wide variety of reservoirs on the market that do not have pre-slit septums or diaphragms. Further, the manufacture of devices containing pre-slit septums or diaphragms tends to be more expensive and complicated than for their slit-less counterparts.

Hypodermic needles have, of course, been utilized for years to conveniently and cost effectively transfer fluid between two reservoirs. To that end, a number of different types of reservoirs have been fashioned that include an injection site which is sealed by a diaphragm and which can be sealingly pierced by a hypodermic needle. Such reservoirs included evacuated tubes, medication vials, culture media containers, IV lines, wide-sites, catheters and the like. However, hypodermic needles pose serious risks of accidental needlesticks to medical personnel, especially where the needles have been exposed to patient fluids that contain the agents of diseases like hepatitis or AIDS.

It should, therefore, be appreciated that there exists a definite need for a medical coupling device which efficiently and effectively accomplishes fluid transfer from one fluid reservoir to another in a variety of situations in a manner that tends to reduce the risk of this exposure to unwanted diseases, infectious agents, contaminants and the like.

SUMMARY OF THE INVENTION

The present invention, which addresses this need, resides in a medical coupling device for transferring fluid between a first reservoir and a second reservoir having a slit-less diaphragm in a manner that helps to minimize the risk of exposure to the fluid from needlesticks. In this regard, the device has a connector with a port and a blunt cannula in fluid communication with the port which is adapted to puncture the diaphragm. Hence, the first reservoir can be attached in fluid communication with the device via the connector and the slit-less diaphragm on the second reservoir thereby facilitating the transfer of fluid between the reservoirs. Since the use of a pointed cannula or needle is avoided, the risk of accidental needlesticks is reduced even though the device is usable with commercially available reservoirs, such as evacuated tubes, having slit-less diaphragms. The device may be securely attached to the first reservoir utilizing a connector, such as a luer lock connector, thereby minimizing the risk of inadvertent disconnection which can lead to contamination of the sample or loss of the fluid. Furthermore, the device can be equipped with other types of connectors to facilitate use with other types of reservoirs.

In more detailed aspects of the invention, the coupling device may include a shroud of predetermined configuration associated with the connector. This shroud defines a recess for receiving the second reservoir into which the cannula extends. Preferably, the shroud is sized and shaped to matingly receive the second reservoir and to guide the reservoir into the interior of the recess. Thus, the shroud provides protection from touch contamination and reduces the risk of a puncture wound. The side-wall of the shroud may be tapered to facilitate insertion of the reservoir. Further, the tapered side-walls advantageously align and guide the blunt cannula toward the center of the diaphragm on the reservoir. In other detailed aspects of the invention, the shroud is also equipped with raised tabs or recesses on the exterior of the side-walls to provide a more stable gripping surface. The shroud further includes a suction opening which advantageously inhibits formation of an undesirable vacuum in the recess of the shroud which is caused by engagement of the reservoir with the side-walls of the shroud.

In still more detailed aspects of the invention, the blunt cannula is between 14 and 30 gauge and is attached in the center of the shroud and disposed lengthwise along the longitudinal axis of the shroud. In order to minimize the risk of puncture wounds, the blunt end of the cannula is substantially perpendicular to the longitudinal axis of the cannula. Further, the side-walls of the shroud extend beyond the blunt end of the cannula in order to prevent inadvertent contact with the cannula. The cannula is suitably dimensioned such that it can be inserted through the slit-less diaphragm of the reservoir with a minimum of force and without gouging or removing pieces of the diaphragm, that the diaphragm sealingly engage the blunt cannula, that the connection be disengaged with a minimum of effort, and that the diaphragm self-seal upon removal of the blunt cannula.

Other features and advantages of the present invention will become apparent from the following description of the preferred embodiment, taken in conjunction with the accompanying drawings, which illustrate, by way of example, the principles of the invention.

DESCRIPTION OF THE PREFERRED EMBODIMENTS

Figure 1:
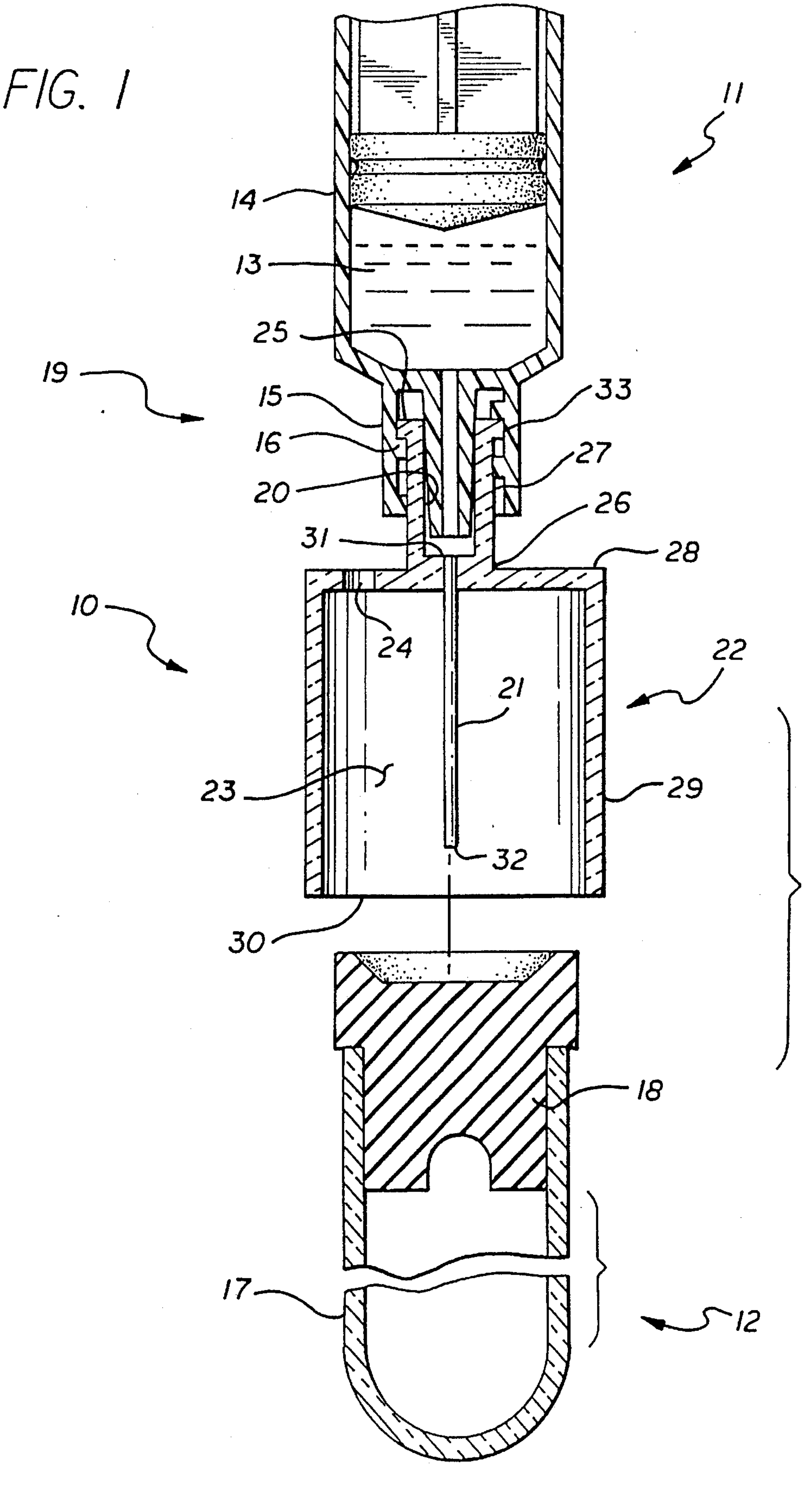
FIG. 1 is a cross-sectional view of a medical connection assembly incorporating a presently preferred embodiment of medical coupling device of the present invention wherein a first reservoir is connected in fluid communication with the coupling device.

With reference now to the exemplary drawings and particularly to FIG. 1 there is shown a medical coupling device 10 interposed between a first and second reservoirs 11 and 12. The first reservoir 11, which contains fluid 13 to be transferred to the second reservoir via the device 10, is a syringe 14 of conventional construction. The syringe 14 can be equipped with a tubular connector 15 having an internal thread 16 commonly known as a "luer lock" connector such that the first reservoir is more securely attached to the device.

The second reservoir 12 is an evacuated tube 17 having a tubular body which is closed at one end and open at the other end. The open end is sealed by a gas impermeable diaphragm 18 which maintains the pressure in the internal cavity of the evacuated tube at a reduced level. Evacuated tubes 17 of this type are marketed under the trade names Vacutainer (manufactured by Becton Dickinson Inc.), Venoject (manufactured by Terumo, Inc.), and Celite (manufactured by Hemocron, Inc.), among others, and are used in numerous medical applications. Typically, these evacuated tubes are constructed of glass or plastic with latex rubber diaphragms. In some evacuated tubes, however, an additional barrier, such as an aluminum foil film, is placed over the open end of the evacuated tube.

The medical coupling device 10 is particularly dimensioned for interposition between reservoirs 11 and 12 and permits fluid to be transferred between reservoir 11 and reservoir 12 in a manner that tends to minimize the risk of exposure to the fluid from needlesticks. The device includes a connector 19 with a port 20, a blunt cannula 21 in fluid communication with the port 20, and a generally cylindrical hollow shroud 22 defining a recess 23 and a suction opening 24. The connector 19 may be manufactured either as a separate part which is attached to the shroud 22 in a conventional manner (See FIG. 1), or as a single piece of unitary construction with the shroud 22. The connector 19 comprises a generally cylindrical tubular portion having a first end 25, a second end 26, and a side-wall 27 defining a port 20. The first end 25 of the connector 19 includes outwardly flared raised tabs 33 on its circumference of known construction, commonly identified as a "luer lock" connector, which engage the internal threads 16 of the tubular connector 15 on the syringe 14. Thus, the connector 19 can be lockingly and sealably engaged with a mating internal thread 16 of the "luer lock" connector 15 of the syringe 14.

Figure 2:
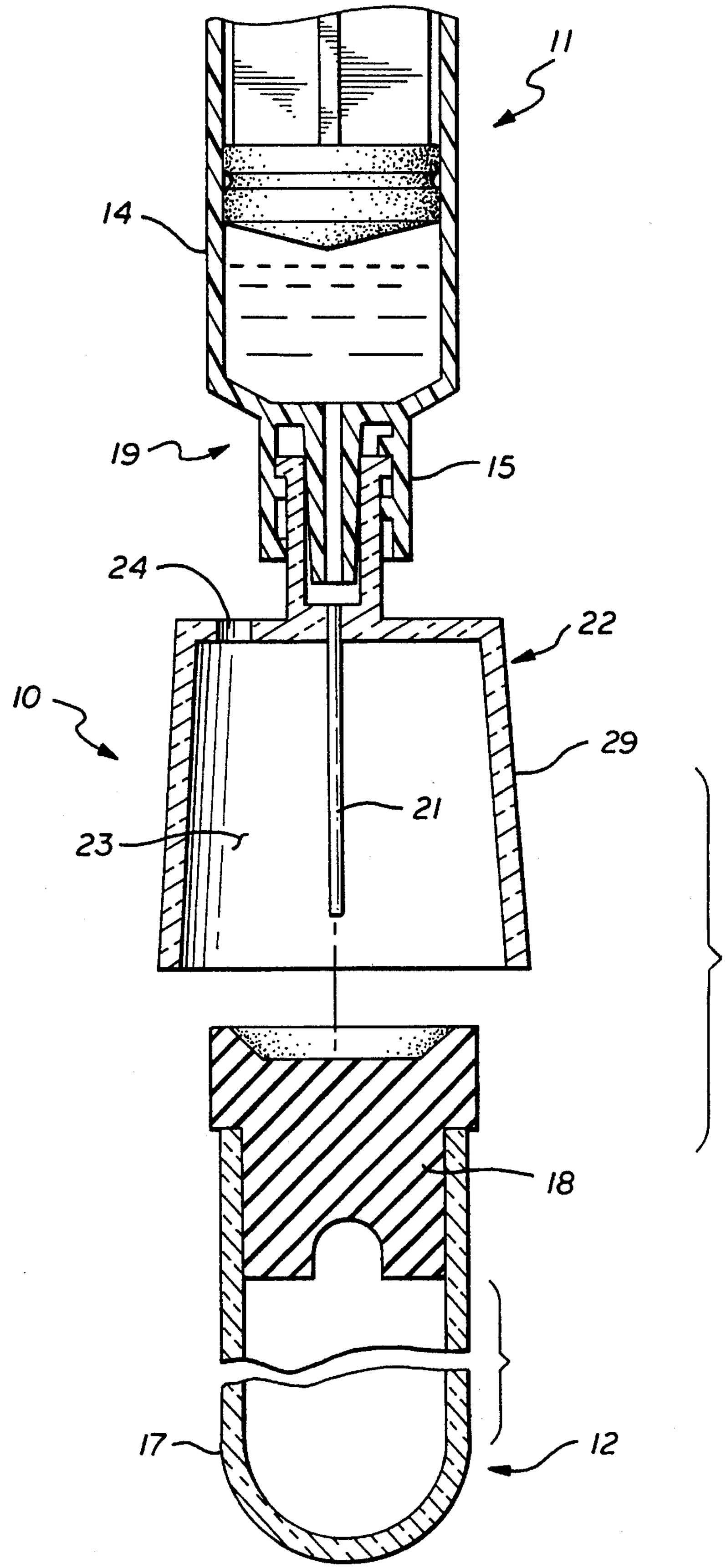
FIG. 2 is a cross-sectional view of the medical connection assembly shown in FIG. 1 with an alternative embodiment of the coupling device which includes a protective shroud with tapered side-walls.

Alternatively, the connector shown in FIGS. 1 and 2 can be sealably mated with a first reservoir 11, such as a syringe, having a tapered cylindrical tube known as a "slip-tip" connector. The first reservoir can be inserted into the port 20 and friction fit against the inner portion of the side-wall 27 of the connector 19.

Utilization of connector 19 makes the device 10 compatible with reservoirs having "luer lock" or "slip-tip" connectors which are both generally accepted standards in the health care industry. The "luer lock" connector advantageously provides a locking engagement that better prevents the possibility of contamination or loss of fluid which may occur if the device is inadvertently disconnected from the reservoir. It will, however, be appreciated that the present invention contemplates the use of reservoirs equipped with other types of connectors. Accordingly, the connector 19 can be adapted for use with such connectors.

The shroud 22 provides protection from touch contamination and reduces the risk of a puncture wound. It includes a base 28 and a substantially cylindrical side-wall 29 which defines the cylindrical recess 23 and an opening 30 through which the reservoir is received. The shroud 22 is also advantageously sized and shaped to matingly receive the reservoir 12 and to guide the reservoir 12 into the interior of the recess 23.

The side-wall 29 of the shroud 22 is also tapered so that the opening 30 is suitably dimensioned for the reservoir 12 to be moved easily into the device. (See, FIG. 2) Thus, as the reservoir 12 is inserted by a user into the opening of the shroud 22, the reservoir 12 is inherently aligned by the side-wall 29. Further, the blunt cannula 21 is guided toward the center of the diaphragm 18 of the reservoir 12 where it punctures the diaphragm. In order to facilitate manual combination of the device 10 and the reservoir 12, the device can also be equipped with raised tabs or recesses on the exterior of the side-walls 29 of the shroud 22 which would provide a more stable gripping surface.

The suction opening 24 is defined in the base 28 of the shroud 22 and advantageously prevents the formation of an undesirable vacuum in the recess 23 of the shroud 22 caused by engagement of the reservoir 12 with the side-walls 29 of the shroud. It will be understood that, although in the preferred embodiment shown in FIG. 1 the shroud 22 and reservoir 12 both have a generally cylindrical shape, the present invention can be adapted to reservoirs of varying shapes and configurations. The length of commercially available evacuated tubes generally ranges from 3" to 5".

Thus, it is desirable that the shroud 22 be sized so that a portion of the evacuated tube 17 extends beyond the opening 30 in the shroud 22 when the evacuated tube 17 has been inserted into the shroud 22.

For the purpose of reducing the risks of fluid contamination caused by a puncture wound, the cannula 21 is blunt and suitably dimensioned such that it can be inserted through the slit-less diaphragm 18 of the evacuated tube 17. When so inserted, it effectively causes the syringe 14 to be in fluid communication with the reservoir 12 through the device. The cannula 21 through which fluid flows is a hollow thin tube having a first end 31 and a blunt second end 32 and is preferably constructed of a metal, such as aluminum or steel, but can also be made of conventional medical grade plastic. The first end 31 of the cannula is attached to the base 28 of the shroud 22 so that the cannula is in fluid communication with the port 20. The cannula 21 may terminate near the base 28 of the shroud 22 or, alternatively, extend through the base 28 of the shroud 22 into the port 20. Preferably, the cannula 21 is attached at the center of the base 28 of the shroud 22 and disposed lengthwise along the longitudinal axis of the recess 23. It will also be observed that the side-walls 29 of the shroud 22 extend beyond the second end 32 of the blunt cannula 21 in order to further prevent inadvertent contact with the cannula 21.

Figure 3:
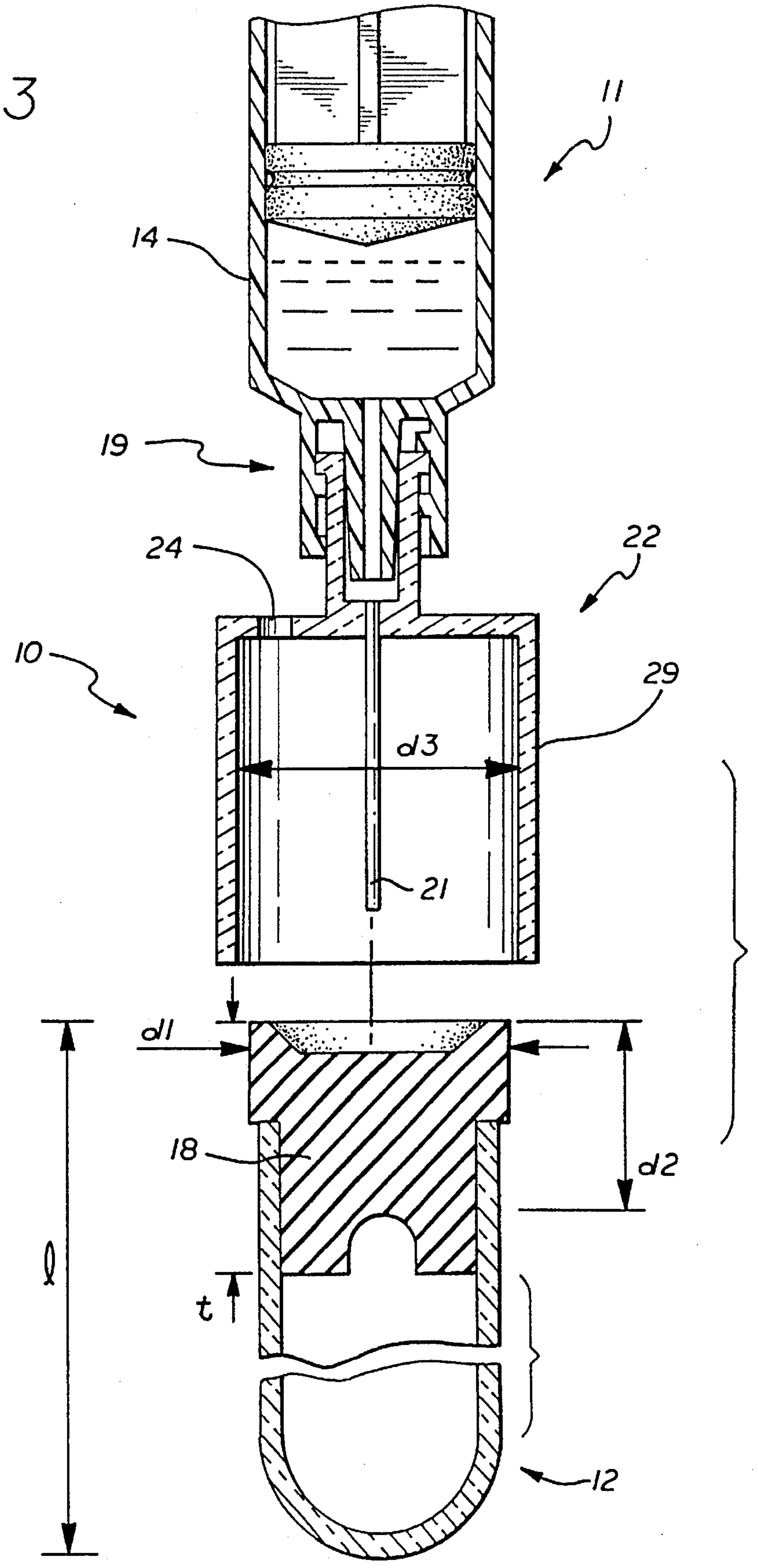
FIG. 3 is a cross-sectional view of the medical connection assembly shown in FIG. 1 setting forth certain dimensional characteristics of the assembly which may be taken into consideration in determining the size and shape of the coupling device.

In determining the size and shape of the device, particularly the blunt cannula 21 and shroud 22, to be utilized in combination with the reservoir 12, several considerations are taken into account. With reference to FIG. 3, these include the shape of the reservoir, its length 1, its diameter d1, and the material and thickness t of the diaphragm 18. A further consideration is the distance d2 which must be traversed by second end 32 of the cannula before the second end 32 of the cannula gains access to the interior cavity of the reservoir.

Since commercially available reservoirs, such as evacuated tubes, are generally cylindrical in shape, a cylindrical shroud of sufficient diameter with substantially parallel side-walls will accommodate a cylindrical tube. The diameter d1 of these evacuated tubes generally ranges from approximately 11 mm to 18.25 mm. The diameter d3 of the shroud 22 is preferably large enough so that the desired evacuated tube 17 can be easily and conveniently inserted into the recess 23 of the shroud 22. If it is desirable that the device be compatible with a wider variety of evacuated tubes, the device can be equipped with a shroud 22 with a diameter slightly larger than that of the largest reservoir for which use is anticipated.

Figures 4A, 4B, 4C:
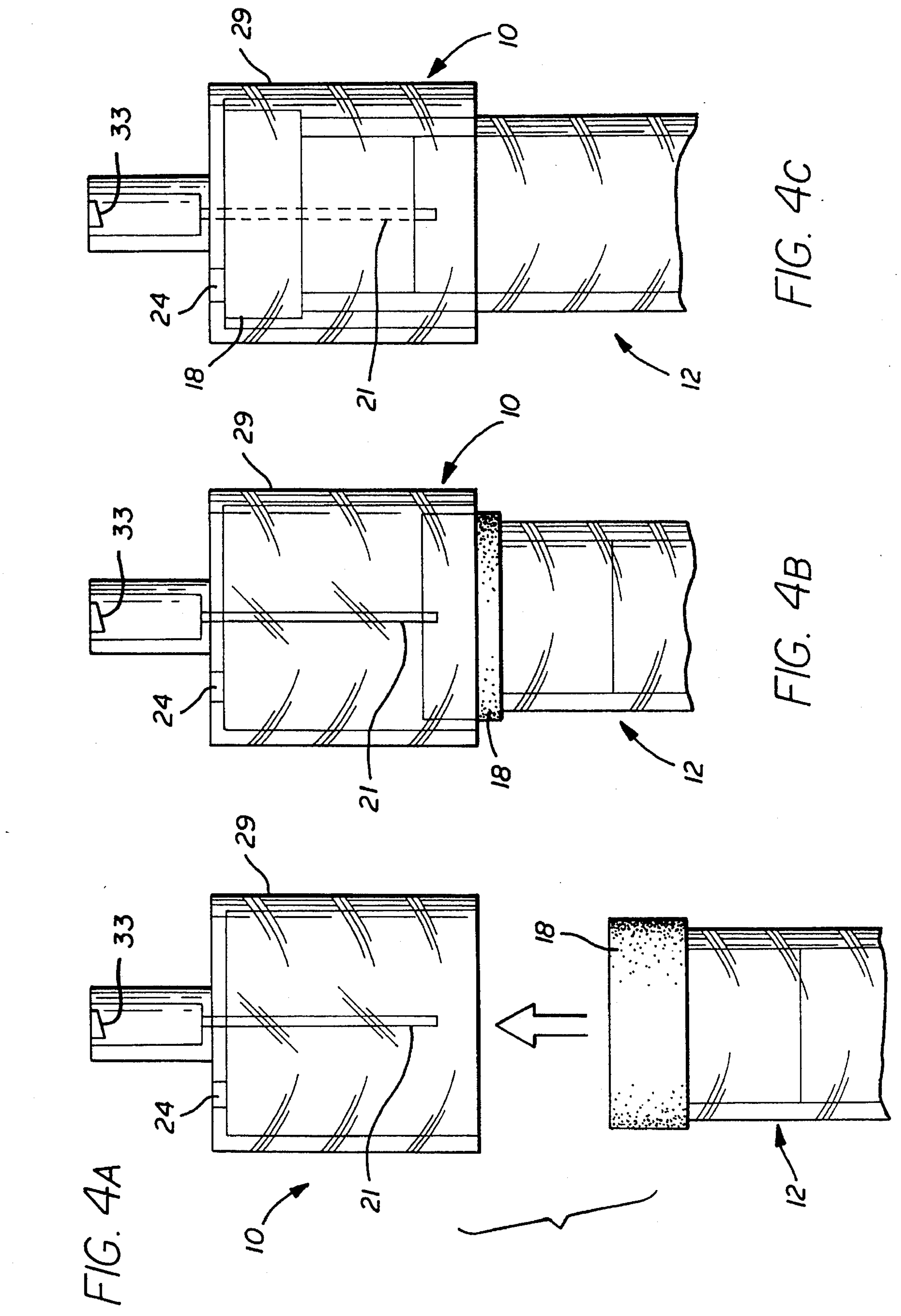
FIGS. 4A–C are a series of elevational views showing the sequential steps by which the medical coupling device of the present invention is connected in fluid communication with a reservoir having a slit-less diaphragm.

As shown in FIG. 4, the blunt cannula 21 is of sufficient length that its second end 32 extends into the internal cavity in the reservoir 12 once the cannula punctures the diaphragm 18. In commercially available reservoirs such as evacuated tubes, the distance d2 that the cannula must traverse before it gains access to the interior cavity generally ranges from approximately 8.5 mm to 12.5 mm. In such tubes, a blunt cannula of approximately 15 mm is preferably utilized. In other types of commercially available evacuated tubes, the distance d2 may be as short as 2 mm. If the device 10 is intended for use with such tubes, a shorter blunt cannula may be appropriate.

The particular diameter of the cannula 21 is advantageously selected so that the cannula punctures the diaphragm 18 with a minimum of force without gouging or removing pieces of the diaphragm, that the diaphragm 18 sealingly engages the cannula that the connection is disengaged with a minimum of effort, and that the diaphragm self-seals upon removal of the cannula. It will be understood that the material and thickness of the diaphragm 18 will be a primary consideration in selecting this diameter. In this regard, the thickness t of the diaphragm 18 at the center of commercially available evacuated tubes generally ranges from approximately 1 mm to 6.5 mm. Therefore, a 14–30 gauge metal cannula with a second end 32 substantially perpendicular to a longitudinal axis extending through the cannula has been found to be appropriate. Within this range, a 19 gauge metal cannula has been found to be particularly appropriate. As the gauge of the cannula 21 is reduced, the cannula becomes larger in circumference and is more likely to gouge or remove pieces of the diaphragm 18 thereby affecting the integrity of the diaphragm and the seal. As the gauge of the cannula 21 is increased, the circumference of the cannula decreases and the cannula may more easily puncture the diaphragm. Typically, however, as the gauge increases, the throughput of the cannula decreases and the cannula has a greater tendency to clog.

The connector 19 and cannula 21 may be constructed of medical grade plastic materials. Preferably, the plastic will be optically transparent so that the user can observe the cannula 21 engage and puncture the slit-less diaphragm 18 of the reservoir 12. In this case, the device may be of unitary construction.

Referring to FIG. 4, the method by which a transfer of fluid between a reservoir 11 and reservoir 12 having an injection site with a slit-less diaphragm 18 will now be discussed. For the purpose of connecting the device 10 and reservoir 11 in fluid communication with the reservoir 12, the reservoir 12 is aligned with the opening 30 in the shroud 22 and inserted into the recess 23 of the shroud 22. As the reservoir 12 is inserted, the side-walls 29 of the shroud 22 engage the reservoir 12 and slit-less diaphragm 18 thereby guiding the reservoir into the interior of the recess 23, centering the evacuated tube 17 within the recess 23, and bringing the slit-less diaphragm 18 into contact with the blunt cannula 21. As the reservoir 12 is inserted further into the recess 23, the centrally mounted blunt cannula 21 punctures the slit-less diaphragm 18 and extends into the internal cavity of the reservoir 12, thereby connecting the first reservoir 11 in fluid communication with the second reservoir 12.

In order to disconnect the device 10 from the reservoir 12, the user grips the exposed end of the reservoir 12 and the device 10 or reservoir 11 and manually disengages the cannula 21 from the diaphragm 18 of the reservoir 12. Thereafter, the device 10 can be used to transfer fluid between the reservoir 11 and another reservoir or the reservoir 11 can be disengaged and the device 10 discarded.

It will also be appreciated that the device 10 can be utilized to transfer fluid from the second reservoir 12 to the first reservoir 11. For example, where the reservoir 12 is an evacuated tube 17 and the reservoir 11 is a syringe 14, the user could utilize the coupling device 10 connect the reservoirs in fluid communication and then use the syringe 14 to aspirate and collect fluid contained in the evacuated tube 17. It will also be appreciated that the device 10 or reservoir 12 can be equipped with a locking mechanism which would engage and lock the pieces together once the blunt cannula 21 has punctured the diaphragm 18, thereby preventing the reservoir 12 from being accidentally disconnected from the coupling device 10.

Moreover, selection of the reservoir is often dictated by the application to which the present invention is applied. In the case where it is desirable to obtain or transfer a sample of blood, any catheter placed in the circulatory system will be a potential source of fluid which could be sampled by aspiration with a syringe equipped with the device of the present invention. Thereafter, the fluid could be delivered to an evacuated tube. For example, a syringe connected in fluid communication with a device of the present invention could be used to aspirate blood from a Hickman, Broviak, Mahurkar, Central Venous, Swan-Ganz, or arterial line catheter. This sample could then be transferred to a reservoir such as an evacuated tube, culture media container, or the like.

Further, although a particular form of the invention has been illustrated and described, it will be appreciated by those skilled in the art that various modifications can be made without departing from the spirit and scope of the invention. Accordingly, the scope of the present invention is not to be limited by the particular embodiments above, but is to be defined only by the appended claims and equivalents thereof.

I claim:

1. A medical coupling device for transferring a fluid between a first reservoir and a second reservoir having a slit-less diaphragm, comprising:

a connector having a port; and a blunt cannula in fluid communication with the port and adapted to puncture and sealingly engage the diaphragm and thereby transfer fluid between the first reservoir and the second reservoir.

2. A medical coupling device according to claim 1, wherein:

the device further includes a shroud of predetermined configuration associated with the connector and defining a recess for receiving the second reservoir; and the cannula extends within the recess.

3. A medical coupling device according to claim 2, wherein the shroud defines a suction opening.

4. A medical coupling device according to claim 2, wherein the association resides in the shroud being formed integrally with the connector.

5. A medical coupling device according to claim 2, wherein the shroud defines a tapered sidewall for aligning the reservoir with the cannula and guiding the cannula into contact with the diaphragm.

6. A medical coupling device according to claim 2, wherein the cannula is connected to the shroud.

7. A medical coupling device according to claim 1, wherein the cannula is a hollow tube having an end which is substantially perpendicular to an axis extending longitudinally through the tube.

8. A medical coupling device according to claim 1, wherein the cannula is between 14 and 30 gauge.

9. A medical coupling device according to claim 1, wherein the connector is a luer lock connector.

10. A medical coupling device according to claim 1, wherein the connector is a slip-tip connector.

11. A medical coupling device for transferring a fluid between a first reservoir and a second reservoir having a slit-less diaphragm, comprising:

a connector having a port;

a blunt cannula in fluid communication with the port and adapted to puncture and sealingly engage the diaphragm and thereby transfer fluid between the first reservoir and the second reservoir; and a shroud of predetermined configuration associated with the connector and defining a recess for receiving the second reservoir, the cannula extending within the recess.

12. A medical coupling device according to claim 11, wherein the shroud defines a suction opening.

13. A medical coupling device according to claim 11, wherein the association resides in the shroud being formed integrally with the connector.

14. A medical coupling device according to claim 11, wherein the shroud defines a tapered sidewall for aligning the reservoir with the cannula and guiding the cannula into contact with the diaphragm.

15. A medical coupling device according to claim 11, wherein the cannula is connected to the shroud.

16. A medical coupling device according to claim 11, wherein the cannula is a hollow tube having an end which is substantially perpendicular to an axis extending longitudinally through the tube.

17. A medical coupling device according to claim 11, wherein the cannula is between 14–30 gauge.

18. A medical coupling device according to claim 11, wherein the connector is a luer lock connector.

19. A medical coupling device according to claim 11, wherein the connector is a slip-tip connector.

20. The medical coupling device according to claim 11, wherein:

the shroud defines a suction opening and a tapered sidewall for aligning the second reservoir with the cannula and guiding the cannula into contact with the diaphragm; and the cannula is a hollow tube connected to the connector with an end which is substantially perpendicular to an axis extending longitudinally through the tube.

21. The medical coupling device of claim 20, wherein the cannula is between 14 and 30 gauge.

22. A medical coupling device for transferring a fluid between a first reservoir and a second reservoir having a slit-less diaphragm, comprising:

a connector having a port;

a blunt cannula of between 14 and 30 gauge in fluid communication with the port and adapted to puncture and sealingly engage the diaphragm and thereby transfer fluid between the first reservoir and the second reservoir; and a shroud defining a recess for receiving the second reservoir, and a suction opening, the shroud further being associated with the connector and having a tapered sidewall for aligning the second reservoir with the cannula and guiding the cannula into contact with the diaphragm.

* * * * *